(12) United States Patent
Hell

(10) Patent No.: US 7,224,452 B2
(45) Date of Patent: May 29, 2007

(54) METHOD OF EXCITING MOLECULES OUT OF A FIRST STATE INTO A SECOND STATES USING AN OPTICAL SIGNAL

(75) Inventor: Stefan W. Hell, Göttingen (DE)

(73) Assignee: Max-Planck-Gesellschaft zur Förderung der Wissenschaften e.V., München (DE)

( * ) Notice: Subject to any disclaimer, the term of this patent is extended or adjusted under 35 U.S.C. 154(b) by 0 days.

(21) Appl. No.: 11/525,505

(22) Filed: Sep. 22, 2006

(65) Prior Publication Data

US 2007/0013909 A1    Jan. 18, 2007

Related U.S. Application Data

(63) Continuation of application No. PCT/EP2005/003228, filed on Mar. 26, 2005.

(51) Int. Cl.
*G01N 21/64* (2006.01)

(52) U.S. Cl. .................. 356/317; 356/36; 250/458.1

(58) Field of Classification Search ............. 356/36, 356/317, 318, 417; 250/458.1, 459.1, 461.1, 250/461.2
See application file for complete search history.

(56) References Cited

U.S. PATENT DOCUMENTS 4,942,134 A * 7/1990 Winefordner et al. ...... 436/161

5,034,613 A    7/1991 Denk et al.

FOREIGN PATENT DOCUMENTS

| DE | 101 54 699 A1 | 5/2003 |
|---|---|---|
| WO | WO 98/40723 | 9/1998 |
| WO | WO 03/029817 A2 | 4/2003 |

OTHER PUBLICATIONS

Hell, Stefan W., "Toward Flourescence Nanoscopy", Nature Biotechnology, vol. 21, No. 11, Nov. 2003, pp. 1347-1355.

(Continued)

*Primary Examiner*—F. L. Evans
(74) *Attorney, Agent, or Firm*—Thomas, Kayden, Horstemeyer & Risley, LLP

(57) ABSTRACT

In a fluorescence-microscopic method of examining a sample with high spatial resolution, the sample is first cooled to a temperature of below 5° C.; next the cooled sample is transferred out of a ground state into a fluorescent state within an area captured by a detector using an excitation beam of light; next the cooled sample is subject to de-excitation of excited molecules by stimulated emission in the area captured by the detector, except at desired measuring points, using an de-exciting beam of light, the de-exciting beam of light having a spatial intensity distribution comprising a zero point located at the desired measuring points, and the excited sample being transferred back into its ground state by the de-exciting beam of light; and then fluorescence light spontaneously emitted by the cooled sample is measured with the detector, the detector detecting fluorescence light that is emitted only from the measuring points.

30 Claims, 2 Drawing Sheets

OTHER PUBLICATIONS

Jasny, Jan, et al., "Fluorescence Microscopy in Superfluid Helium: Single . . . ", Am. Inst. of Physics, Rev. Sci. Instr. 67 (4), Apr. 1996 (XP-002291592), pp. 1425-1430.

Vacha, Martin, et al., "Laser Scanning Microscope for Low Temperature Single Molecule and Microscale Spectroscopy . . . ", 1999 Am. Inst. of Physics (XP-000875397), pp. 2041-2045.

Segura, J.m, et al., "A Sample-Scanning Confocal Optical Microscope for Cryogenic Operation", 2000 Am. Inst. of Physics, (XP-001063829), pp. 1706-1711.

Dyba, Marcus, et al., "Focal Spots of Size N23 OPen Up Far-Field Florescence Microscopy . . . ", 2002 Am. Physical Society, (XP-001097237), pp. 163901-1 to 163901-4.

* cited by examiner

METHOD OF EXCITING MOLECULES OUT OF A FIRST STATE INTO A SECOND STATES USING AN OPTICAL SIGNAL

CROSS REFERENCE TO RELATED APPLICATIONS

This application is a continuation of the international patent application PCT/EP2005/003228 filed Mar. 26, 2005, entitled "Verfahren zur Anregung der Moleküle von einem ersten Zustand in einen zweiten Zustand mit einem optischen Signal" (English translation: "Method for exciting Molecules in a first State into a second State using an optical Signal") and claiming priority to European Patent Application No. EP 04 007 533.5, filed Mar. 29, 2004 and having the same title as the international patent application

FIELD OF THE INVENTION

The present invention generally relates to a method of transferring a sample out of a first state into a second state using an optical signal. Particularly the present invention relates to such methods in which the optical signal has a spatial intensity distribution having at least one zero point and areas adjacent to the zero point in which the intensity of the optical signal is such high that a saturation is achieved in transferring the sample into the second state.

BACKGROUND OF THE INVENTION

A Method of transferring a sample out of a first state into a second state using an optical signal is known from German patent application DE 101 54 699 A1. For investigating a sample by fluorescence microscopy, the fluorescence marker molecules in the sample are first brought into an excited energy state using an exciting optical signal. With regard to this optical excitation the usual limit for spatial resolution in optical methods of $\lambda/2n$ applies, wherein $\lambda$ is the wavelengths of the light used and n is the diffraction index of the sample. To improve the spatial resolution beyond this limit, the optically excited state is depleted with a de-exciting optical signal everywhere in the sample, except at desired measuring points in which the de-exciting optical signal intensity distribution features a local zero. For example, the fluorescence marker molecules in the sample are quenched by stimulated emission using the de-exciting optical signal. This is the case outside the measuring point where the de-excitation optical signal is not zero or not close to zero. The dimensions of the resulting fluorescent measuring point, i.e. the spatial resolution of the remaining fluorescence, can be reduced much below the common optical resolution limit, in that the de-exciting optical signal is applied to the sample outside the desired measuring point at such an intensity that a saturation is achieved in depleting the fluorescent energy state by stimulated emission. Thus, the fluorescent marker molecules in the sample are in the fluorescent state only in a very narrowly limited area around the zero point of the intensity distribution of the de-exciting optical signal. According to the publication Hell, Nature Biotechn., 21, 1347–1355, the size of the fluorescent measuring point $\Delta x$ and thus the spatial resolution follow $\Delta x \approx \lambda/(2n\sqrt{I/I_s})$, wherein $\lambda$ is the wavelengths, n is the diffraction index, I is the applied intensity and $I_s$ is the saturation intensity. The saturation intensity is the characteristic intensity at which the sample is de-excited by 50% because of the influence of the de-exciting optical signal from a probabilistic point of view. The saturation intensity $I_s$ is inversely proportional to the cross-section $\sigma$ of the de-exciting optical signal according to $I_s=1/(\sigma\tau)$. Here, $\tau$ is the average life time for which the sample remains in the excited state, before it spontaneously decays into the de-excited state. As a result, the following applies to the resolution $\Delta x \approx \lambda/(2n\sqrt{I\sigma\tau})$. Thus for achieving a high resolution it is advantageous to work with an intensity of the de-exciting optical signal that is as strong as possible, with a cross-section $\sigma$ that is as large as possible and with a fluorescent state featuring a life time $\tau$ that is long enough.

Maximizing the intensity of the de-exciting optical signal, which is required for achieving the saturation, there is the danger, that the sample is chemically modified. Such a chemical modification, as a rule, is caused by a formation of radicals due to the strong light intensities, which enable various chemical reactions. Particularly, if oxygen and other reactive species are in the sample, the de-exciting optical signal causes undesired chemical reactions that are known as "photobleaching" when they affect the fluorescence dye in the sample. The intensity of the de-exciting optical signal necessary for saturation could be reduced, if the cross-section $\sigma$ could be increased.

However, it is often necessary to work at a wavelength of the de-exciting optical signal at which $\sigma$ is comparatively low. The reason is that at another, often shorter wave length at which the cross-section would be higher, other undesired processes would be initiated besides the desired de-excitation. These other processes would interfere with the desired de-excitation of the marker molecules in the sample, like for example, they would excite the sample into the excited fluorescent state again so that the overall efficiency of the desired de-excitation would be decreased.

The lifetime $\tau$ of a certain excited fluorescent state is generally fixed.

From J. Jasny et al.: "Fluorescence microscopy in superfluid helium: single molecule imaging" Re. Sci. Instrum 67 (4), April 1996, pages 1425–1430 it is known that low temperatures (of about 2 K) in detection and spectroscopy of single molecules have the result that the full width at half maximum of the absorption line from a ground state to the lowest excited singlet state of the observed molecule becomes so narrow that it reaches the limits set by its natural lifetime. As a result, environmental influences on the molecule result in a shift of the absorption line of much more than its full width at half maximum. Observing the line thus allows for spectroscopic monitoring of various environmental influences on the molecule.

A need still exists for a method of fluorescence-microscopically investigating a biological sample at high spatial resolution without damaging the sample with the high intensities of the de-exciting optical signal.

SUMMARY OF THE INVENTION

In one aspect the present invention provides a method of transferring a sample out of a first state into a second state using an optical signal, the method comprising the steps of cooling the sample to a temperature of below 5° C.; and of applying the optical signal to the cooled sample, the optical signal having an intensity distribution with at least one zero point and with areas which are located adjacent to the at least one zero point and in which the intensity of the signal is so high that a saturation in transferring the sample into the second state is achieved.

In a more particular aspect the present invention provides a fluorescence-microscopic method of examining a sample with high spatial resolution, the method comprising the steps of cooling the sample to a temperature of below 0° C.; of transferring the cooled sample out of a ground state into a fluorescent state within an area captured by a detector using an excitation beam of light; of de-exciting excited molecules in the sample by stimulated emission, using a de-exciting beam of light that is applied in the measurement area of the detector, but not at a desired measuring point, the de-exciting beam of light having a spatial intensity distribution comprising a zero point located at the desired measuring point, and the excited sample being transferred back into its ground state by the emission stimulated by the de-exciting beam of light; and of measuring fluorescence light spontaneously emitted by the cooled sample with the detector, the detector detecting fluorescence light emitted from the measuring point only.

In an even more particular aspect the present invention provides a fluorescence-microscopic method of examining a viable biological sample with high spatial resolution, the method comprising the steps of cooling the sample to a temperature of below 150 K under a protection gas atmosphere, which is basically free of water vapor and of any other gas species condensing at the temperature of the cooled sample; of transferring the cooled sample under the protection gas atmosphere out of a ground state into a fluorescent state within an area captured by a detector using an excitation beam of light; of selecting a wavelength of a de-exciting beam of light with regard to a maximum cross section for stimulating the sample for emission of fluorescence light; of exciting the cooled sample under the protection gas atmosphere for stimulated emission of fluorescence light in the area captured by the detector except of a desired measuring point using he de-exciting beam of light, the de-exciting beam of light having a spatial intensity distribution comprising a zero point located at the desired measuring point, and the excited sample being transferred back into its ground state by the emission stimulated by the de-exciting beam of light; of measuring fluorescence light spontaneously emitted by the cooled sample under the protection gas atmosphere with the detector, the detector detecting fluorescence light emitted out of the measuring point only; of heating the sample to a temperature at which it lives again for a certain interval of time; and of repeating the previous steps for fluorescence-microscopically examining the biological sample having progressed in live.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the attached drawings. The components in the drawings are not necessarily to scale, emphasis instead being placed upon clearly illustrating the principles of the present invention. In the drawings, like reference numerals designate corresponding objects throughout the several diagrams.

DETAILED DESCRIPTION OF THE INVENTION

Figure 1:
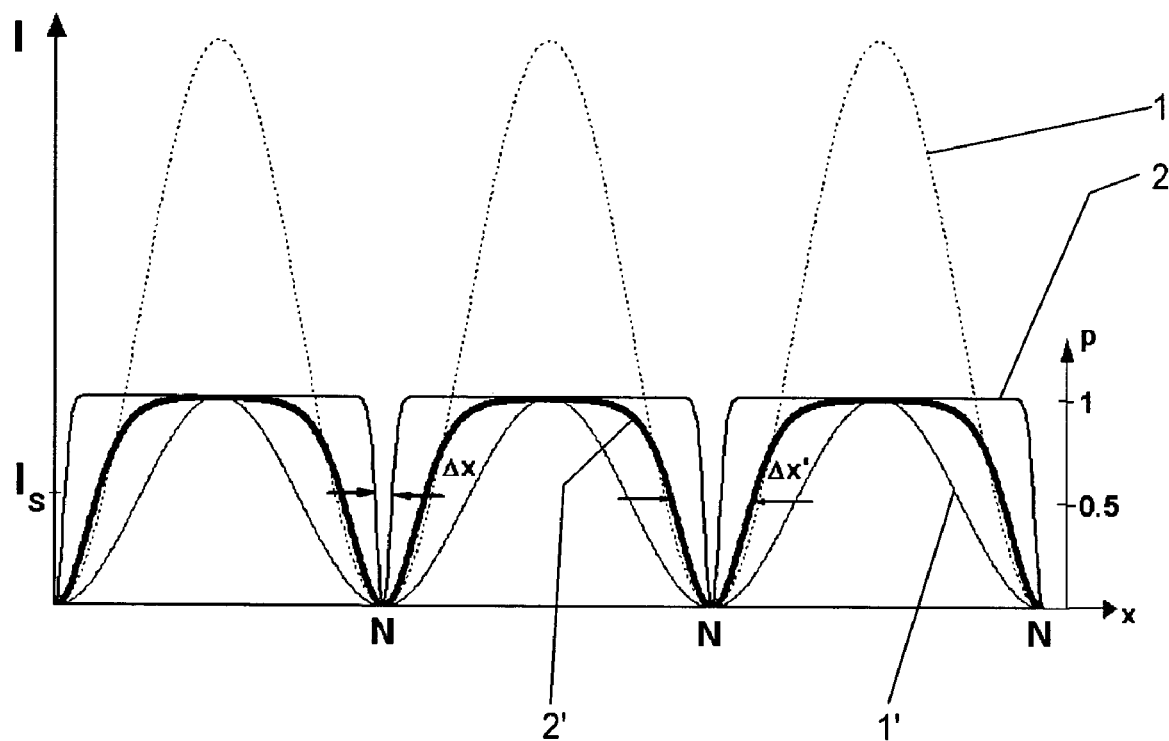
FIG. 1 is a graph of the spatial intensity distribution of an optical signal and the resulting transfer probabilities of a sample out of a first state into a second state.

In the new method the sample is cooled down below at least 5° C. before the optical signal is applied. Already by cooling down below 5° C. a relevant immobilization of the single components of the sample is achieved as compared to a sample at room temperature. Particularly, toxic agents which could be transformed into radicals by high intensities of the optical signal, are no longer mobile within the sample to such an extent that they could cause damages in a bigger spatial area. Even with high intensities of the optical signal any damages by toxic agents remain local. Thus, cooling the sample below 5° C. already shows a clear effect reducing the bleaching under the influence of the optical signal, particularly with water containing samples, i.e. with all biological samples. Below 5° C. the dipoles of the water molecules start to align. The motility of the water molecules and of any substance dissolved in the water decreases. To the same extent to which the tendency of the sample towards chemical modifications under the influence of the optical signal is reduced by cooling the sample, the intensity of the optical signal can be increased to increase the spatial resolution of the areas of the sample, which are left in the first state, according to $\Delta x \approx \lambda/(2n\sqrt{I/I_s})$ in that the saturation of the sample with the first signal gets closer to the zero points of the intensity distribution of the first signal because the overall intensity of the first signal is increased.

From the field of analyzing substances by optical spectroscopy it is generally known that cooling to low temperatures inhibits or at least slows down bleaching under the influence of an optical probe beam. Here, however, there is no requirement, that the intensity distribution of an optical signal has to be above the saturation intensity of the sample to achieve a maximum spatial resolution. Thus, there is no correlation between the spatial resolution and the temperature in optical spectroscopy, even if the spatial resolution may be of interest.

With water-containing samples it is particularly preferred to cool them to a temperature of at least 0° C. before the optical signal is applied. I. e. it is preferred to freeze the samples, ideally in a so-called quick-freezing process in which the sample is quickly dipped in a cooling liquid to avoid the formation of ice crystals. Freezing under formation of amorphous ice considerably decreases the motility of the reactive components of the sample, and thus the possible spatial extent of chemical modifications caused by the influence of the optical signal, even if the intensity of the first signal is strongly increased for increasing the spatial resolution.

If the sample is definitely cooled down below 0° C., this results in further advantages. The distribution of the energy states in which the sample is present before the optical signal is applied, clearly changes. Thermally excited states are de-populated and may completely disappear. Thus, the sample is in a more defined state prior to applying the optical signal. The main reason for the low cross sections of the optical signals with saturating intensities used in the prior art is that the sample is not in a definitely excited or definitely de-excited state at room temperature but that the population of its states are thermally distributed in sub-states according to the Bolzmann-distribution. Thus, for example in fluorescence-microscopy at room temperature, the fluorescence dye Pyridine 2 has to be de-excited via stimulated emission at a wave lengths of 760 nm, although the emission spectrum, featuring a maximum at 670 nm, indicates an optimum de-excitation in the wavelength range between 690 to 740 nm. If it would be tried to de-excite the fluorescence dye Pyridine 2 in the 690–740 nm range at room temperature, this would not only result in de-excitation but also in re-excitation of the dye to its fluorescent state. As a result, the strong cross-sections for the de-excitation cannot be used effectively. The thermal split-up of the energy states precludes the optical signal to act unambiguously in the spectral range where the cross-section for stimulated emission is large. However, if according to the present invention the thermal excitation of the sample is reduced, the thermal split-up of the population of the energy states decreases, and thus, the wavelength of the optical signal can be selectively tuned to a wavelength entailing large cross-sections for the desired transfer of the sample out of the first into the second state. Even with a constant intensity of the optical signal this has a direct positive effect on the obtained spatial resolution. With an additional increase of the intensity, which is possible because of the reduced tendency of the sample to undergo chemical modifications at low temperatures, the spatial resolution is further increased.

Additionally, thermally induced transfers of the sample are reduced, like for example an undesired nonradiative relaxations of the excited first state. This has the result that the lifetime $\tau$ of the first state is significantly increased, which according to the formula $\Delta x \approx \lambda/(2n\sqrt{I\sigma\tau})$ also results in an increased spatial resolution.

Upon cooling the sample to a temperature below 150 K the thermal influence on the population of the sub-energy states, which is represented by the Bolzmann-factor, $e^{-\Delta E/kT}$ is reduced to less than one tenth as compared to room temperature. In a fluorescence dye, the population of vibrational and rotational states decrease with decreasing temperature. Thus, further reductions of the thermal influences result from a further reduction of the temperature of the sample. A temperature of below 80 K can be achieved by cooling with liquid nitrogen. A temperature of below 5 K can be realized by cooling with liquid helium. At temperatures of below 5 K, thermal broadenings of the energy states of the sample have virtually disappeared.

Particularly, if the state of the sample is to be changed with the optical signal at very low temperature it has to be cared for that the environment of the sample is suited for these low temperatures. This often requires that the sample is kept under a protection gas atmosphere when the optical signal is applied, which protection gas atmosphere is free of water and other substances which may condensate at low temperatures. Further, it is of course also desired that the protection gas atmosphere does not comprise any reactive substances, like for example oxygen, which accelerate a bleaching of the sample under the influence of the optical signal.

In a particularly preferred embodiment of the new method, the sample is kept in a vacuum when the optical signal is applied, to care for optimum conditions. A vacuum also means a good thermal isolation of the sample. The level of the vacuum in optical methods, however, does not need to be as high as in electron microscopy, for example, where any molecules in the path of the electron beam are to be avoided.

Because of the given equation for the obtainable spatial resolution, all embodiments of the new method are of particular interest, in which the wavelength of the optical signal is optimized with regard to its cross-section for transferring the sample out of the first into the second state. In the new method, this optimization is particularly also possible, when the first state is an excited energy state of the sample in which it has been previously transferred by means of a further optical signal, the second state being an again de-excited energy state. The sharper definition of the energy states of the sample—its sub-states are less populated— caused by the low temperatures clearly decreases the undesired probability that the optical signal not only transfers the sample out of the first into the second state, but undesirably also causes a transfer of parts of the sample back into the excited first state.

Particularly, the new method can be applied in fluorescence microscopy, the excited state being a fluorescent state of a fluorescence marker in a sample.

In a particularly preferred embodiment of the present invention, the sample is a living or viable biological sample. This sample is quickly cooled down to the reduced temperature at which its present state of live is frozen-in and at which the sample can be fluorescence-microscopically examined according to the new method without initiating photochemical processes in the sample which could affect its viability. The biological sample can rather be heated up to a temperature at which its life progresses after its fluorescence-microscopic examination. Like the cooling of the biological sample, the heating should occur as quickly as possible, but without partially over-heating the biologic sample. Heating the sample up to a life-compatible temperature can be affected by electro-magnetically irradiating the sample like, for example, with IR-light or microwaves. Preferably, the electro-magnetic irradiation for heating up the sample again is selected in such a way that it does not selectively excite the fluorescence dye, which would be associated with the danger of bleaching the fluorescence dye. When the steps of cooling down, of fluorescence-microscopically examining and heating up the biologic sample are repeated at such intervals of time that the sample can live on and develop further in between, the fluorescence-microscopically taken images of the sample represent a series of snapshots and hence represent the process of life in slow motion.

Preferred enhancements of the invention are provided by the dependent patent claims and the whole description. Further features of the invention can be found in the drawings. The combinations of features of different embodiments of the invention or features of different claims independent of the selected dependencies are also possible and proposed. This also applies to such features, which are depicted in separate drawings or mentioned in the description of separate drawings. These features may also be combined with features of different claims.

Referring now to FIG. 1 in which the intensity I is plotted over the place of application of an optical signal 1, the distribution of the intensity I is sinusoidal and comprises the zero points denominated by N. $I_s$ is the characteristic intensity at which the sample under the influence of the de-exciting optical signal 1 is de-excited by 50% from a statistics point of view. At an intensity larger than $I(p=1) = 3 \times I_s$ the optical signal 1 causes that the marker molecules in the sample are virtually completely transferred out of its second state into its first state. The comparatively strong absolute intensity of the optical signal 1 causes that the probability p at which the sample is in the second state has a distribution 2 which is also depicted in FIG. 1 and which approaches unity everywhere outside the zero points N of the optical signal. In other words, saturation is achieved in transferring the sample out of its first into its second state with the optical signal 1 everywhere outside the zero points N of its spatial intensity distribution. The spatial extent $\Delta x \approx \lambda/(2n\sqrt{I/I_s})$ of the areas of the sample around the zero points N of the optical signal 1, in which the sample still is in the first state, is clearly narrower than the spatial resolution $\lambda/2n$ which is achieved in usual optical applications. The spatial extent of the areas of the sample, which are still in the first state around the zero points N however, quickly decreases with increasing intensity I of the optical signal 1, which is clearly apparent from a reduced optical signal 1' and a corresponding distribution 2' resulting in a dimension $\Delta x'$, which are also depicted in FIG. 1. The first state of the sample can be the energy ground state $S_0$ of a dye molecule with the optical signal exciting the sample into the second state, like for example the fluorescent state $S_1$.

Figure 2:
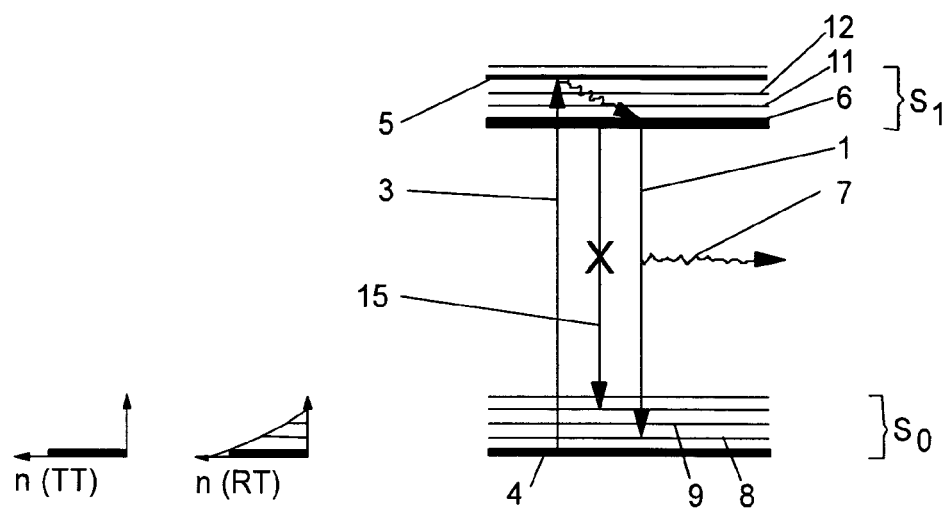
FIG. 2 shows an energy spectrum of a fluorescence dye together with a depiction of populations of sub states of its ground state at room temperature and at low temperature.

Another particular application of the optical signal 1 which has been explained with reference to FIG. 1 is the field of fluorescence microscopy in which a fluorescence dye is de-excited out of an excited first state by means of stimulated emission except of a measuring point of interest. FIG. 2 schematically indicates both the first state, i.e. the energetically excited state $S_1$, as well as the second state, which is the energetic ground stat $S_0$ here, as well as their respective sub-division into vibrational sub-states, each of which additionally comprising a fine-structure not depicted here. Prior to applying the optical signal 1, the sample is first transferred out of a sub-state 4, which is a lower vibrational sub-state of the ground state $S_0$, by means of a further optical signal 3 into a sub-state 5, which is a vibrational sub-state of the electronically excited state $S_1$. Out of the sub-state 5, the excited fluorescence dye gets into the sub-state 6, or at a temperature above absolute zero according to the Bolzmann statistics into a thermally excited, slightly higher sub-state 11. Both 6 and 11 are excited states out of which the fluorescence dye can spontaneously get back into the second state, i.e. in the electronic ground state $S_0$, upon emission of fluorescence light 7. The de-excitation on the sub state 8 of the ground state $S_0$ is stimulated by optical signal 1 everywhere outside the actual measuring point of interest, which has a slightly lower quantum-energy than the optical signal 3, so that during the subsequent measurement the fluorescence dye only remains in the fluorescent sub-states 6 or 11 within a measuring points corresponding to one of the zero points N of the optical signal 1. Thus, fluorescence light registered during the subsequent measurement can only originate from the measuring point which has been reduced in its spatial dimensions by application of the optical signal 1. The thermal excitation of the fluorescence dye, the energy spectrum of which is indicated in FIG. 2, has the result that a plurality of vibrational sub-states, i.e. of higher sub-states of the second state, may be populated, such as the sub-states 8, 9 and 10, as well as higher vibrational sub states of the first state, like for example the sub-states 11, 12 and 5 I. e. the dye molecules do not have a sharply defined energy when it is in one of these states but energies within an interval which increases in size with increasing temperature. This is indicated in FIG. 2 in that the populations of the sub-states of the ground state $S_0$ are schematically depicted at room temperature RT and at low temperature TT. Whereas at room temperature a plurality of vibration sub-states has a relevant population, only the ground state itself is populated at low temperature.

Because of the broadening of the population of sub-states with increasing temperature, the probability increases that a de-excitation by stimulated emission effected by the first optical signal 1 also results in an unwanted excitation of the fluorescence dye out of the sub-state 8 and/or the sub-state 9 into the excited sub-states 6 or 11. On the other hand, the excitation of the fluorescence dye with the second optical signal 3 may also result in an unwanted de-excitation by stimulated emission out of the sub-state 5, 11 or 12 back into the sub-state 4, and thus reduce the fluorescence signal originating from the limited spatial areas of the sample which are to be measured. The two functions which are assigned to the two optical signals, i.e. de-exciting the fluorescence dye out of the first state and exciting the fluorescence dye into the first state, respectively, can thus not be achieved with the unambiguousness desired.

In addition, with increasing temperature the probability increases that upon emission of fluorescence light 7 according to FIG. 2, the dye does not get back out of its sub-state 6 into the ground state $S_0$, but due to a transfer of momentum it gets to its sub-state 10. The more the process 15 competes with the spontaneous fluorescence out of the sub-state 6, the shorter is the lifetime of the sub-state 6. The shorter the lifetime of the sub-state 6, the stronger must be the intensities by which this fluorescent sub-state can be removed outside the zero points N of the spatial distribution of the optical signal 1 according to FIG. 1 during the lifetime of the first state, in order to be able to measure the sample by its spontaneous fluorescence out of the first state only in the zero points N according to FIG. 1. If, however, the lifetime of the fluorescent sub-state 6 is in turn increased by decreasing the temperature, the intensity of the optical signal 1 can be reduced, or the spatial resolution can be increased according to $\Delta x \approx \lambda/(2n\sqrt{I\sigma\tau})$. What has been said in this paragraph with regard to sub-state 6 also applies to the slightly higher sub-state 11.

Figure 3:
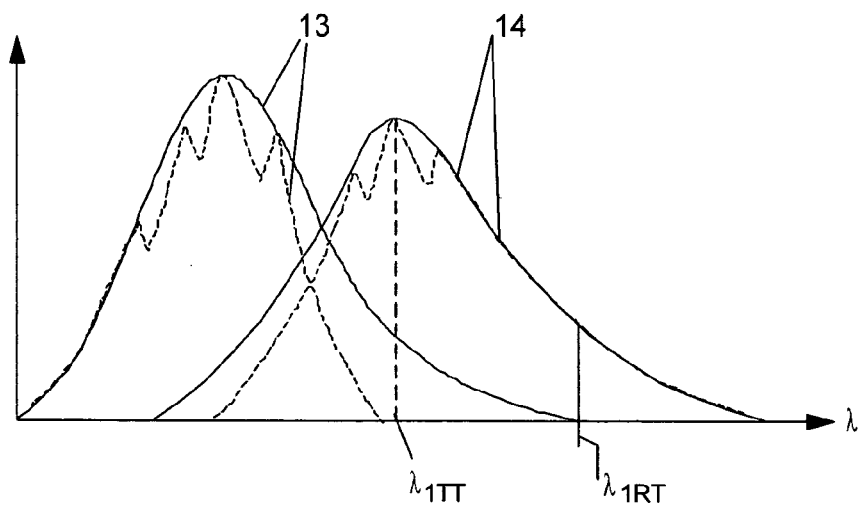
FIG. 3 shows the cross-sections of two optical signals with regard to the fluorescence dye according to FIG. 2 at room temperature and at low temperature.

FIG. 3 illustrates why reducing the population of the higher sub-states according to FIG. 2 also results in the opportunity to reduce the intensity of the optical signal 1 required for the saturation in transferring the sample out of a first sub state 6 into its second sub state 8 outside the area of the zero points N, or to increase the cross section $\sigma$ and thus the spatial resolution. Referring now in detail to FIG. 3, the absorption spectrum 13 and the emission spectrum 14 of a typical dye are plotted versus the wavelength $\lambda$ of the optical signal 1 and of the further optical signal 3. Here, the continuous lines qualitatively indicate the curves of the spectra versus the wavelength $\lambda$ at room temperature, and the dashed lines qualitatively indicate the curves at a temperature below 80 K. Each of the peaks of the spectra, which are broad at room temperature, contracts in the direction of the $\lambda$-axis, and single partial peaks become visible at low temperature, which mainly belong to vibrational sub states. Particularly, the overlapping of the excitation and the emission spectrum in the middle of both spectra along the $\lambda$-axis decreases. The emission spectrum largely scales with the cross section $\sigma$ for the stimulated emission. Whereas at room temperature the optical signal 1 has to have a wavelength $\lambda_{1RT}$ in order to be effective for de-excitation by stimulated emission and to not concomitantly undesirably excite the dye, at lower temperature the de-excitation optical signal 1 can have the wavelength $\lambda_{1TT}$. At the latter wavelength the cross section for stimulated emission is larger than the cross section at at $\lambda_{1RT}$. $\lambda_{1TT}$ typically is by more than 10 nm smaller than $\lambda_{1RT}$. This directly results in a better resolution, i.e. smaller $\Delta x$ or, as an alternative, it is possible to reduce the intensity of the de-exciting optical signal 1, by which the sample is to be de-excited outside the zero points of its intensity distribution at a saturation level.

At the same time, cooling the sample reduces the motility of radicals, which are produced by the optical signal 1 applied at a high intensity and which with time result in bleaching the sample, because of chemical modifications of the fluorescence marker molecules in the sample. Thus, the intensity I of the optical signal can be increased for increasing the spatial resolution at lower temperature without increasing the tendency towards bleaching.

In the new method, the combination of the various effects based on the temperature decrease results in a considerable potential for increasing the spatial resolution without bleaching the dyes contained in the sample. This potential can particularly be used in fluorescence microscopy.

Many variations and modifications may be made to the preferred embodiments of the invention without departing substantially from the spirit and principles of the invention. All such modifications and variations are intended to be included herein within the scope of the present invention, as defined by the following claims.

I claim:

1. A method of transferring a sample out of a first state into a second state using an optical signal, the method comprising the steps of:
cooling the sample to a temperature of below 5° C.; and
applying the optical signal to the cooled sample, the optical signal having an intensity distribution with at least one zero point and with areas which are located adjacent to the at least one zero point and in which the intensity of the signal is so high that a saturation in transferring the sample into the second state is achieved.

2. The method of claim 1, wherein the sample is cooled to a temperature of at least 0° C. prior to applying the optical signal.

3. The method of claim 1, wherein the sample is cooled to a temperature of below 150 K prior to applying the optical signal.

4. The method of claim 1, wherein the sample is cooled to a temperature of below 80 K prior to applying the optical signal.

5. The method of claim 1, wherein the sample is cooled to a temperature of below 5 K prior to applying the optical signal.

6. The method of claim 1, wherein the sample is kept under a protection gas atmosphere while cooling it and while applying the optical signal.

7. The method of claim 6, wherein the protection gas atmosphere is free of water and free of any species condensing at the temperature of the cooled sample.

8. The method of claim 1, wherein the sample is kept under vacuum while cooling it and while applying the optical signal.

9. The method of claim 1, comprising the further step of selecting a wavelength of the optical signal with regard to a maximum cross section for transferring the sample out of the first state into the second state.

10. The method of claim 1, comprising the further steps of exciting the sample into the first state, which is an excited energy state of the sample, using a further optical signal, and de-exciting the sample out of the first state into the second state by means of the optical signal.

11. The method of claim 10, wherein the excited state is a fluorescent state of a fluorescent dye.

12. A fluorescence-microscopic method of examining a sample with high spatial resolution, the method comprising the steps of:
cooling the sample to a temperature of below 5° C.;
transferring the cooled sample out of a ground state into a fluorescent state within an area captured by a detector using an excitation beam of light;
exciting the cooled sample for stimulated emission of fluorescence light in the area captured by the detector except of a desired measuring point using an de-exciting beam of light,
the de-exciting beam of light having a spatial intensity distribution comprising one or more zeros located at the desired measuring points, and
the excited sample being transferred back into its ground state by the de-exciting beam of light; and
measuring fluorescence light spontaneously emitted by the cooled sample with the detector,
the detector detecting fluorescence light emitted out of the measuring points only.

13. The method of claim 12, wherein the sample is cooled to a temperature of at least 0° C. prior to applying the optical signal.

14. The method of claim 12, wherein the sample is cooled to a temperature of below 150 K prior to applying the optical signal.

15. The method of claim 12, wherein the sample is cooled to a temperature of below 80 K prior to applying the optical signal.

16. The method of claim 12, wherein the sample is cooled to a temperature of below 5 K prior to applying the optical signal.

17. The method of claim 12, wherein the sample is kept under a protection gas atmosphere while cooling it and while applying the optical signal.

18. The method of claim 17, wherein the protection gas atmosphere is free of water and free of any species condensing at the temperature of the cooled sample.

19. The method of claim 12, wherein the sample is kept under vacuum while cooling it and while applying the optical signal.

20. The method of claim 12, comprising the further step of selecting a wavelength of the de-exciting beam of light with regard to a maximum cross section for stimulating the sample for the emission of fluorescence light.

21. The method according to claim 12, wherein the sample is a viable biological sample.

22. The method according to claim 20, comprising the further steps of
heating the sample to a temperature at which it lives again for a certain interval of time; and
repeating the previous steps for fluorescence-microscopically examining the biological sample having progressed in life.

23. The method of claim 22, wherein the biologic sample is heated up again by electro-magnetic irradiation.

24. The method of claim 23, wherein the biological sample is heated up again by electro-magnetic irradiation selected from a group consisting of IR-light and microwaves.

25. A fluorescence-microscopic method of examining a viable biological sample with high spatial resolution, the method comprising the steps of
cooling the sample to a temperature of not higher than 0° C. under a protection gas atmosphere, which is free of water vapor and free of any species condensing at the temperature of the cooled sample;
transferring the cooled sample under the protection gas atmosphere out of a ground state into a fluorescent state within an area captured by a detector using an excitation beam of light;
selecting a wavelength of a de-exciting beam of light with regard to a maximum cross section for stimulating the sample for emission of fluorescence light;

generating with the de-exciting beam of light stimulated emission for molecular de-excitation under the protection gas atmosphere in the area captured by the detector in the cooled sample except of at the location of a desired measuring point, the de-exciting beam of light having a spatial intensity distribution comprising one or more zeros located at the desired measuring points, and the excited sample being transferred back into its ground state by the emission stimulated by the de-exciting beam of light;

measuring with the detector fluorescence light emitted by the cooled sample under the protection gas atmosphere, the detector detecting fluorescence light that is emitted just from the measuring point;

heating the sample to a temperature at which it lives again for a certain interval of time; and repeating the previous steps for fluorescence-microscopically examining the biological sample having progressed in life.

26. The method of claim 25, wherein the sample is cooled to a temperature of below 150 K prior to applying the optical signal.

27. The method of claim 25, wherein the sample is cooled to a temperature of below 80 K prior to applying the optical signal.

28. The method of claim 25, wherein the sample is cooled to a temperature of below 5 K prior to applying the optical signal.

29. The method of claim 25, wherein the biologic sample is heated up again by electro-magnetic irradiation.

30. The method of claim 29, wherein the biologic sample is heated up again by electro-magnetic irradiation selected from a group consisting of IR-light and microwaves.

* * * * *